(12) United States Patent
Chen et al.

(10) Patent No.: US 11,529,382 B2
(45) Date of Patent: Dec. 20, 2022

(54) *LACTOBACILLUS FERMENTUM* STRAIN V3 AND ITS EFFICACIES OF INTESTINAL MICROFLORA REGULATION, ANTI-INFLAMMATION AND CANCER PREVENTION (71) Applicant: Syngen Biotech. Co., Ltd., Tainan (TW)

(72) Inventors: Wei-Jen Chen, Tainan (TW); Shiuan-Huei Wu, Tainan (TW); Chiau-Ling Gung, Tainan (TW); Yu-Lun Tsai, Tainan (TW)

(73) Assignee: SYNGEN BIOTECH. CO., LTD., Tainan (TW)

( * ) Notice: Subject to any disclaimer, the term of this patent is extended or adjusted under 35 U.S.C. 154(b) by 0 days.

(21) Appl. No.: 16/938,358

(22) Filed: Jul. 24, 2020

(65) Prior Publication Data

US 2021/0023149 A1 Jan. 28, 2021

(30) Foreign Application Priority Data

Jul. 24, 2019 (TW) .................................. 108126214

(51) Int. Cl.
| | |
|---|---|
| *A61K 35/747* | (2015.01) |
| *C12N 1/20* | (2006.01) |
| *A61P 29/00* | (2006.01) |
| *A61P 35/00* | (2006.01) |
| *C12R 1/225* | (2006.01) |

(52) U.S. Cl.
CPC ............ *A61K 35/747* (2013.01); *A61P 29/00* (2018.01); *A61P 35/00* (2018.01); *C12N 1/20* (2013.01); *C12N 1/205* (2021.05); *C12R 2001/225* (2021.05)

(58) Field of Classification Search
None
See application file for complete search history.

(56) References Cited

PUBLICATIONS

Chatterjee et al. Cancer Immunol Immunother. 1994 38:75-82).*
Yaghoubi et al. BBA Reviews on Cancer. 1874 (2020) 188388 pp. 1-17.*
Chakraborty et al. ecancer 2012, 6:ed16 DOI:10.3332/ecancer.2012.ed16.*
Corcos et al. Cancer Medicine 2013; 2(4):421-426.*
Ferreira, Daniela & Adega, Filomena & Chaves, Raquel. (2013). The Importance of Cancer Cell Lines as in vitro Models in Cancer Methylome Analysis and Anticancer Drugs Testing. 10.5772/1745.*

\* cited by examiner

*Primary Examiner* — Oluwatosin A Ogunbiyi
(74) *Attorney, Agent, or Firm* — Birch, Stewart, Kolasch & Birch, LLP (57) ABSTRACT

The present invention provides a novel *Lactobacillus fermentum* strain, named *Lactobacillus fermentum* strain V3, and its use in manufacturing a pharmaceutical composition or a food composition for regulating intestinal microflora and treating and/or preventing an inflammatory diseases and/or a cancer.

5 Claims, 7 Drawing Sheets
(3 of 7 Drawing Sheet(s) Filed in Color)
Specification includes a Sequence Listing.

LACTOBACILLUS FERMENTUM STRAIN V3 AND ITS EFFICACIES OF INTESTINAL MICROFLORA REGULATION, ANTI-INFLAMMATION AND CANCER PREVENTION

BACKGROUND OF THE INVENTION

Field of the Invention

The present invention relates to a novel *Lactobacillus fermentum* strain and, in particular, to a novel *Lactobacillus fermentum* strain for treating and/or preventing an inflammatory disease and/or a cancer.

Description of the Prior Art

According to estimates, about 20% of colorectal cancer is caused by genetics, and about 80% of colorectal cancer is contributed by factors such as chronic intestinal inflammation, intestinal bacterial flora, etc.

Injection of the mutagenic agent azoxymethane (AOM) to mice and addition of dextran sulfate sodium (DSS) that destroys the large intestinal epithelial cells into mice drinking water cause the intestinal inflammation, and will result in colorectal cancer in about two months. The clinical features of such colorectal cancer caused by the AOM/DSS mouse model are very consistent with that of human colorectal cancer, such as weight loss, hyperplasia of intestinal polyps, etc., so that the AOM/DSS mouse model is a widely used model of colorectal cancer.

In the AOM/DSS mouse model, in addition to intestinal inflammation induced by DSS and colorectal cancer caused by AOM mutation, scientific studies have also confirmed that the changes in the intestinal microflora are significantly related to the formation of colorectal cancer. For example, while AOM/DSS is administrated, oral intake of antibiotics to kill intestinal bacteria can greatly reduce the number of colorectal tumors. In addition, intestinal bacteria associated with colorectal cancer, such as *Porphyromonas*, are known to make intestinal epithelial cells susceptible to bacterial invasion, and Streptococcaceae promotes inflammation of the intestinal tract. It is also found that the number of *Lactobacillus* is negatively correlated with the incidence of colorectal cancer, indicating that the intestinal microflora significantly affects the development of colorectal cancer.

The cell wall component of Gram-negative bacteria, Lipopolysaccharide (LPS), promotes the growth and spread of colorectal cancer cells by promoting the inflammatory response. *Bacteroides fragilis* promotes inflammation and colorectal neoplasia by increasing the permeability of the large intestinal epithelial shield. Enterobacteriaceae excludes anti-inflammatory symbiotic bacteria, such as *F. prausnitzii*, *Bifidobacterium*, etc., to promote colorectal cancer, showing that intestinal inflammation can initiate intestinal tumor formation and accelerate tumor growth rate, which has an adverse effect on colorectal cancer. Scientific research has also confirmed that the inhibition of intestinal inflammation can effectively prevent colorectal cancer and slow down the disease progression of colorectal cancer.

*Lactobacillus* is a common probiotic and is widely used in the production of fermented dairy products. Although the scientific literature has reported that some *Lactobacillus* strains have anti-inflammatory ability, there have been studies showing that the anti-inflammatory active ingredient of *Lactobacillus* is a metabolite of live bacteria. However, the bacterial cells of lactobacilli cannot inhibit secretion of TNF-$\alpha$ inflammatory cytokines by THP-1 caused by LPS no matter whether they are dead or alive, showing that the bacterial cells of lactobacilli do not have anti-inflammatory effects. *Lactobacillus* has low tolerance to stomach acid and choline, and when it reaches the intestine through the digestive system, most of it is dead. Therefore, *Lactobacillus* cannot be metabolized in the intestine to generate enough anti-inflammatory substances. Because the characteristics and abilities of different strains are variable, it is necessary to develop a *lactobacillus* that can inhibit inflammation and colorectal cancer in the inactivated state.

SUMMARY OF THE INVENTION

The present invention is a novel *Lactobacillus fermentum* strain V3 isolated from the microbial flora of dried bamboo shoots and different from the existing known strains. The novel fermented *Lactobacillus* strain of the present invention has the effect of treating or preventing inflammatory diseases or cancer.

Accordingly, in one aspect, the present invention provides an isolated *Lactobacillus fermentum* strain V3 (*Lactobacillus fermentum* V3), which was deposited at Deutsche Sammlung von Mikroorganismen and Zellkulturen GmbH, (Inhoffenstr. 7B, D-38124 Braunschweig), Germany with deposit number DSM33166 on May 28, 2019.

In another aspect, the present invention provides a composition comprising an effective amount of the *Lactobacillus fermentum* strain V3, wherein the isolated *Lactobacillus fermentum* strain V3 is live or dead. The composition may be prepared in the form of a pharmaceutical composition or a food composition, for use in treatment or prevention of an inflammatory disease in a subject, in particular, through inhibition of the production of TNF-$\alpha$ in the subject.

In one embodiment of the invention, the composition is prepared in the form of a pharmaceutical composition or a food composition for treating or preventing an inflammatory disease or a cancer.

In embodiments of the invention, the cancer is selected from the group consisting of colorectal cancer, esophageal cancer and gastric cancer. In one particular embodiment of the invention, the cancer is colorectal cancer.

In a further aspect, the present invention also provides a use of the *Lactobacillus fermentum* strain V3 for preparing a pharmaceutical composition or a food composition for treating or preventing an inflammatory disease or a cancer.

In yet aspect, the present invention further provides a method for treating or preventing an inflammatory disease or a cancer in a subject, comprising administering an effective amount of the *Lactobacillus fermentum* strain V3 to the subject.

BRIEF DESCRIPTION OF THE DRAWINGS

The patent or application file contains at least one color drawing. Copies of this patent or patent application publication with color drawing will be provided by the USPTO upon request and payment of the necessary fee. The foregoing description and the following detailed description of the invention will be better understood when reading in conjunction with the accompanying drawings. For the purpose of illustrating the present invention, currently preferred embodiments are shown in the drawings.

DETAILED DESCRIPTION OF THE EMBODIMENTS

Unless otherwise defined, all technical and scientific terms used herein have the same meaning as commonly understood by those skilled in the art to which the present invention pertains. It should be understood that the terminology used herein is for the purpose of describing specific embodiments only, and is not intended to be limiting.

As used herein, the singular forms "a", "an" and "the" include plural references unless explicitly indicated otherwise. Thus, for example, reference to "a sample" includes a plurality of such samples and their equivalents known to those skilled in the art.

As used herein, the term "colony-forming unit" (CFU) is defined as the number of bacterial cells as revealed by microbial production on an agar medium.

As used herein, the term "treatment" refers to the application or administration of one or more active agents to a subject with a disease, disease symptom, or disease propensity, the purpose of which is to treat, cure, relieve, alleviate, alter, remedy, ameliorate, improve, or affect the disease, disease symptom, or disease propensity. For example, as used herein, "treating an inflammatory disease" refers to the reduction of local or systemic excessive inflammatory responses by inhibiting the expression of TNF-α.

As used herein, the term "effective amount" refers to an amount of an active medicament or composition in a subject sufficient to achieve the above therapeutic efficacy. The effective amount can vary, for example, depending on the type or dosage of the medicament or composition and the weight, age, and health status of the subject to be treated.

The present invention provides an isolated *Lactobacillus fermentum* strain V3 (*Lactobacillus fermentum* V3), which was deposited at Food Industry Research and Development Institute with deposit number BCRC910908 on Jun. 27, 2019, and also at Deutsche Sammlung von Mikroorganismen and Zellkulturen GmbH, Germany with deposit number DSM33166 on May 28, 2019.

The *Lactobacillus fermentum* strain V3 of the present invention was isolated from microbial flora of dried bamboo shoots. According to the analysis of bacteriological characteristics, the strain is a Gram-positive bacterium with a short-rod shape and without spore formation and motility, grows under anaerobic conditions and has no catalase and oxidase activities. Further identification by 16S rDNA sequence analysis shows that the strain V3 is a *Lactobacillus fermentum* strain.

The isolated *Lactobacillus fermentum* strain V3 of the present invention may exist in any manner, including live or dead bacteria, and also includes equivalent strains with the same characteristics and thalli or products derived from said strains.

By using the isolated *Lactobacillus fermentum* strain V3 according to the present invention as a starting material, those skilled in the art can generally obtain other mutants or derivatives thereof by conventional mutation induction or re-separation techniques, and the mutants or derivatives retains or enhances the relevant characteristics and advantages of the strain forming the composition of the invention described herein.

In some embodiments, the composition provided by the present invention has the effect of treating an inflammatory disease. Specifically, as shown in the examples, the composition of the present invention inhibited LPS-induced secretion of TNF-α by THP-1 cells. It was ascertained that the treatment or prevention of inflammatory disease is through the inhibition of the production of TNF-α.

In some embodiments, the composition provided by the present invention has the effect of inhibiting colorectal tumor hyperplasia. Specifically, as shown in the examples, the composition of the present invention can inhibit colorectal cancer caused by mutagen azoxymethane (AOM) and dextran sulfate sodium (DSS), and also has the effect of preventing colorectal tumor proliferation.

In some embodiments, the composition provided by the present invention has the effect of regulating intestinal microflora.

In another aspect, the present invention provides a composition comprising an effective amount of the strain V3 of the present invention for use as a medical product, a medicament, a food, an edible product, a food supplement or a medical food.

The composition of the present invention may be in solid or liquid form, and may especially be in the form of powders, lozenges or buccal tablets, sucking lozenges, film formulations, solutions, aerosols, granules, pills, suspensions, emulsions, capsules, enteric-coated tablets and capsules, syrups, liquids, elixirs, candy, chewable tablets, suppositories, mini-enemas, cream, gel or ointment.

The composition according to the present invention can be formulated into a form in which the strain of the present invention is the only active agent or mixed with one or more other active agents and/or mixed with a pharmaceutically acceptable excipient or sufficient additives or ingredients in the case of food or edible products.

The composition according to the present invention can be manufactured into various types of foods. The products of these foods can be manufactured by any conventional techniques using conventional excipients or fillers, and mixed with additives if necessary.

The composition of the present invention may be manufactured as a food supplement, which may be administered as it is, may be mixed with a suitable drinkable liquid such as water, sour milk, milk or juice, or may be mixed with solid or liquid food. In some embodiments, the food supplement may be in the form of lozenges or buccal tablets, pills, capsules, granules, powders, suspensions, sachets, candy, sticks, syrups and corresponding administration forms, usually in unit dosage form. Preferably, the food supplement including the composition of the present invention is administered in the form of lozenges, buccal tablets, capsules or powders as manufactured in the conventional method for preparing dietary supplements.

The composition of the present invention may be manufactured into various types of medicaments, which may be manufactured by a general pharmaceutical technique or method using a therapeutically effective amount of the composition of the present invention and a pharmaceutically acceptable carrier thereof. Administration of the composition of the present invention includes oral or injection administration, and may further include a pharmaceutically acceptable carrier, a diluent, and/or an excipient. The carrier may be a solvent, a dispersion medium, a coating, an antibacterial agent, an antifungal agent, an isotonic agent, an absorption delaying agent, or the like. The diluent may be bacteriostatic water for injection (BWFI), phosphate buffer, Ringer's solution, glucose solution or the like. The excipient may be calcium carbonate, sodium carbonate, calcium phosphate, sodium phosphate, lactose, starch, gelatin, alginic acid, stearic acid, magnesium stearate or the like.

In yet another aspect, the composition of the present invention provides a use for preventing or treating an inflammatory disease in a subject, wherein non-limiting examples of the inflammatory diseases include inflammatory and autoimmune diseases, such as cancer, Crohn's disease, inflammatory bowel disease (IBD) and inflammatory large intestine disease.

In yet another aspect, the composition of the present invention provides a use for preventing or treating cancer in a subject, wherein the subject is selected from the group of cancers with highly inflammatory conditions. These cancers are also known as having "inflammatory features" and ascending cytokine signaling (e.g., TNF-α). In one embodiment, the cancer is an inflammatory tumor, for example, but not limited to, colorectal cancer, esophageal cancer, and gastric cancer, and especially colorectal cancer.

The above description of the present invention and the following embodiments illustrate the content of the present invention, but are not intended to limit the scope of the present invention.

Example 1 Isolation of *Lactobacillus fermentum* Strain V3

The present invention isolated strains from the microbial flora of dried bamboo shoots, a traditionally fermented food in Taiwan. The dried bamboo shoots were homogenized with addition of sterilized water. After homogenization, the solid was settled by gravity and the liquid portion was sucked up. The liquid was spread on MRS agar (De Man, Rogosa and Sharpe agar) plates and incubated at 37° C. for 3 days, and then a single colony appearing on the agar medium was collected and further purified to isolate the Gram-positive, catalase-negative and rod-shaped and named as *Lactobacillus fermentum* strain V3. The *Lactobacillus fermentum* strain V3 was deposited at Food Industry Research and Development Institute with deposit number BCRC910908 on Jun. 27, 2019, and also at Deutsche Sammlung von Mikroorganismen and Zellkulturen GmbH, Germany with deposit number DSM33166 on May 28, 2019

Example 2 the Bacteriological Characteristics of *Lactobacillus fermentum* Strain V3

Figure 1:
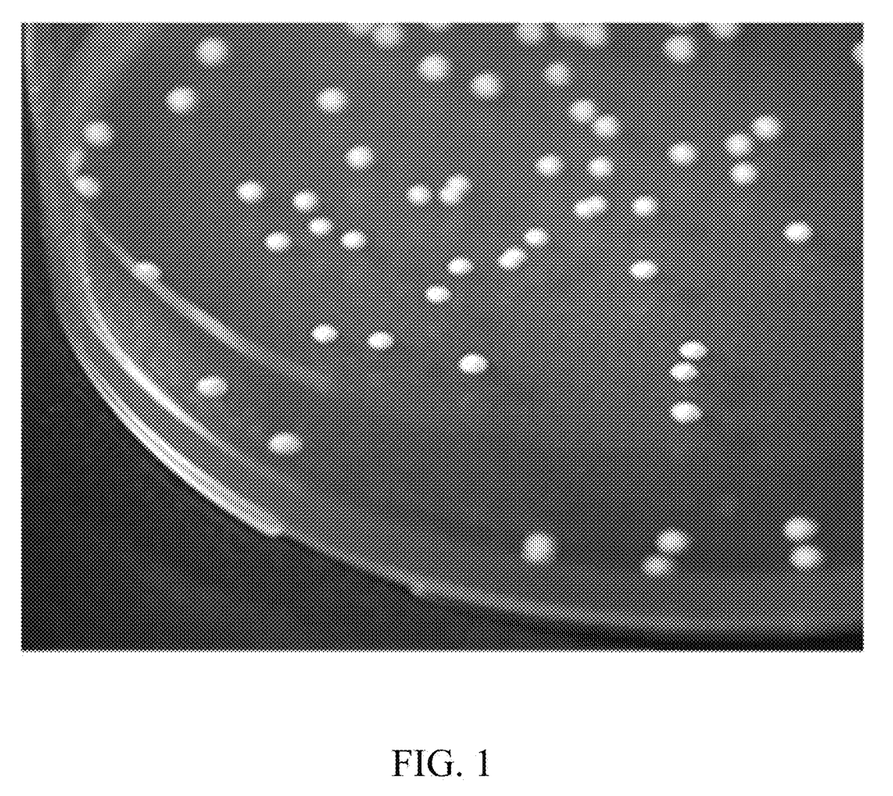
FIG. 1 is an image showing the solid culture appearance of *Lactobacillus fermentum* strain V3.
Figure 2:
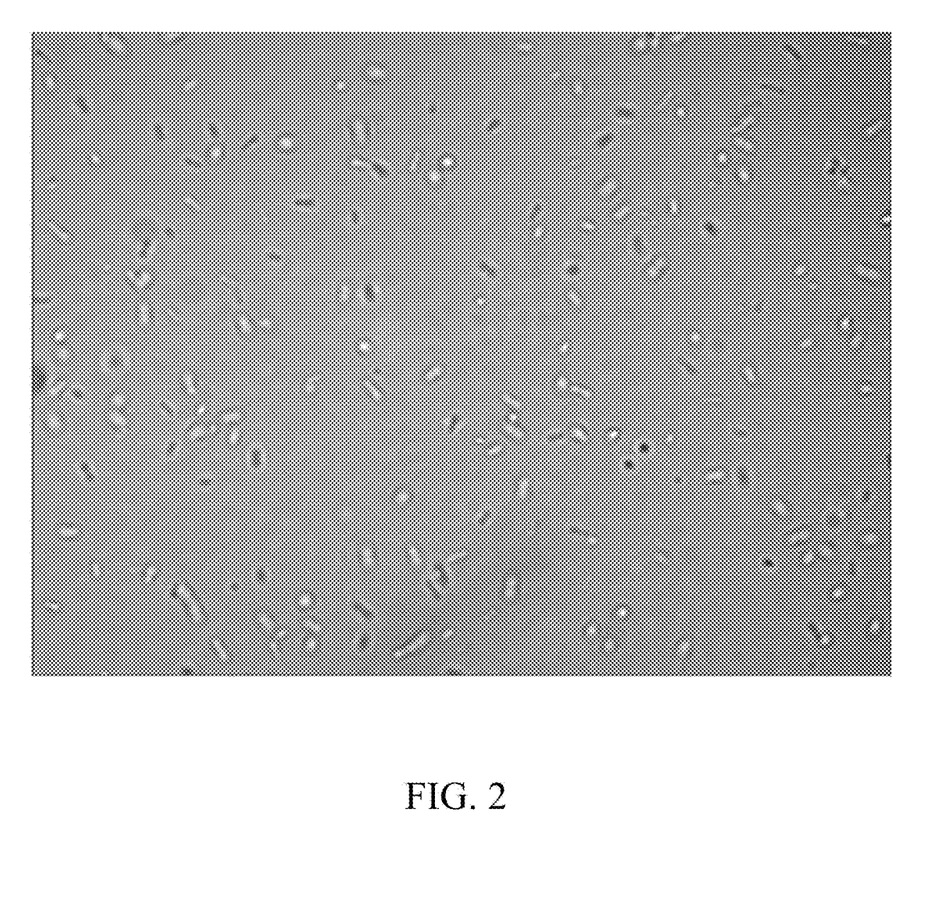
FIG. 2 shows the cell shape of *Lactobacillus fermentum* strain V3.

The strain V3 of the present invention is a Gram-positive, short-rod shaped, non-sporing and non-mobility bacterium, which has typical characteristics of *Lactobacillus*. The bacteriological characteristics of *Lactobacillus fermentum* strain V3 are shown as what follows:

(1) Morphological Characteristics
  (a) Appearance of solid-state culture: After culturing on MRS agar plate for 2 to 3 days, the colony was milky white in appearance, regular in periphery and smooth in surface when being viewed on the plane, and slightly convex when being viewed from the side, as shown in FIG. 1. When being picked with a transplant needle, the single colony had weak cohesion and was easy to disperse.
  (b) Cell shape: After the cells were placed in MRS broth medium and cultured at 37° C. for 24 hours under anaerobic conditions, they can be observed as having a short-rod shape without flagella under the 1500X immersion objective lens of the microscope, as shown in FIG. 2.
  (c) Mobility: No mobility.
  (d) Spore formation: No spore formation.
  (e) Gram stain: Positive.
(2) Characteristics of Culture:
  (a) Medium: MRS broth medium, pH=6.25.
  (b) Culture conditions: at 37° C. under anaerobic conditions.
(3) Physiological Characteristics:
  (a) Catalase: negative.
  (b) Oxidase: negative.

Example 3 16S rDNA Sequencing Analysis of *Lactobacillus fermentum* Strain V3

The DNA of the *Lactobacillus fermentum* strain V3 was extracted to amplify the 16S rDNA (ribosomal DNA) fragment, and agarose gel electrophoresis was performed on the resulting PCR product to confirm whether the product conforms to the expected size and perform sequencing. The 16S rDNA sequence of the resulting *Lactobacillus fermentum* strain V3 was shown as SEQ ID NO:1 and compared with the composite sequence alignment data sets (NCBI blast). The sequence alignment result was closest to *Lactobacillus fermentum*, and the similarity was up to 100%.

Example 4 Inhibition of TNF-α Secretion by *Lactobacillus fermentum* Strain V3

4.1 Preparation of Heat-Inactivated Bacterial Cells of *Lactobacillus fermentum*

Eleven bacterial strains purchased from both Bioresource Collection and Research Center, Food Industry Research and Development Institute (Hsinchu, Taiwan) and the stains as obtained in the present invention were cultured respectively and statically in MRS at 37° C. for 24 hours and then the culture solutions were centrifuged (4000 RCF, 10 minutes). After the supernatant was removed, the remaining was washed with phosphate buffer saline (PBS), and then repeated the centrifugation and wash processes under the same conditions for two times. The bacterial cells suspended in PBS after cleaning were the live bacteria samples (Live). The Live samples were measured for the absorbance value with a spectrophotometer, and then put in a 70° C. water bath for 30 minutes to form the dead bacteria samples (Dead). The prepared dead bacteria samples were inoculated into the MRS culture solution and cultured at 37° C. for two days. As a result, there was no sign of growth, indicating that the bacteria had all died out.

4.2 Design of Cell Experiments

The human mononuclear THP-1 cell line (BCRC 60430) was purchased from Bioresource Collection and Research Center, Food Industry Research and Development Institute (Hsinchu, Taiwan), and cultured in RPMI 1640 broth containing 10% fetal bovine serum, 0.05 mM 2-mercaptoethanol, 10,000 I.U./mL penicillin, 10,000 μg/mL streptomycin and 25 μg/mL amphotericin at 37° C. under 5% $CO_2$. THP-1 cells were inoculated into a 96-well dish at a concentration of $6 \times 10^5$/mL, cultured for 18 hours, and then stimulated with 500 ng/mL LPS for 20 hours in the presence of the heat-inactivated bacterial cells of *Lactobacillus* (the absorbance value being adjusted to a final concentration of $OD_{600}=0.01$). The culture supernatant was collected and analyzed for the content of cytokine TNF-α. For the LPS control group, LPS was added alone for stimulation without the presence of bacterial cells. For the control group, only cell culture fluid was used.

4.3 Inhibition of Secretion of Inflammatory Cytokine TNF-α by *Lactobacillus fermentum* Strain V3

Figure 3:
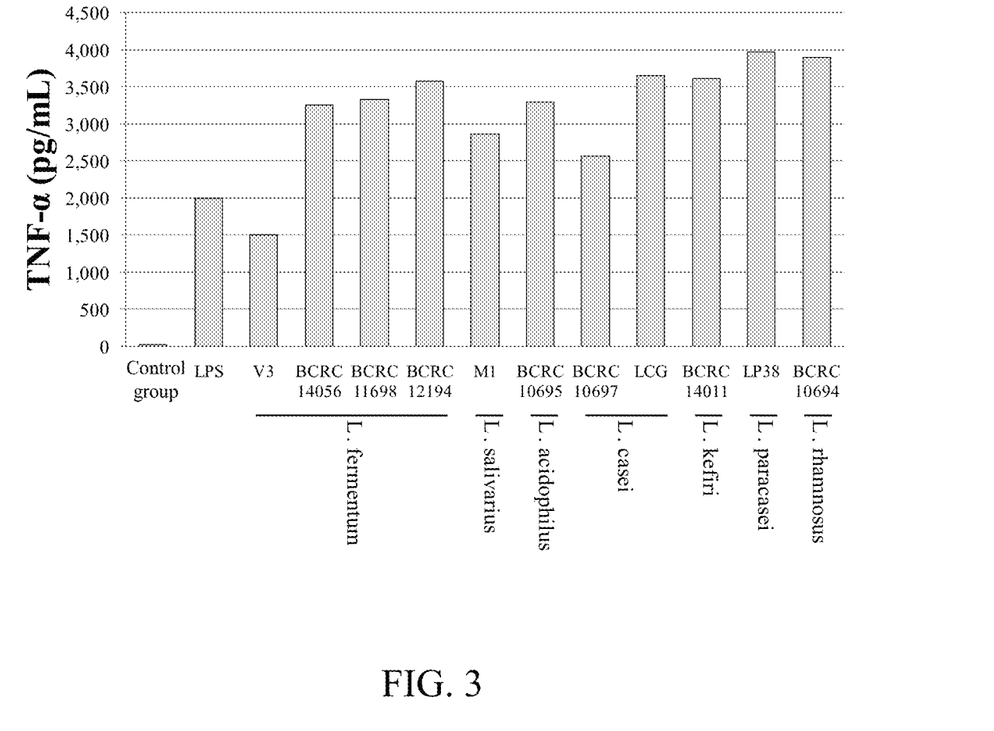
FIG. 3 shows the inhibitory activities of eleven strains of different heat-inactivated bacteria cells on TNF-α secretion.

As shown in FIG. 3, among the eleven strains of different heat-inactivated (dead) bacteria, only *Lactobacillus fermentum* strain V3 inhibited LPS-induced secretion of TNF-α by THP-1 cells, while the remaining 10 strains of the heat-inactivated bacteria all promoted TNF-α secretion, indicating that the heat-inactivated bacteria from V3 possessed anti-inflammatory activities.

Figure 4:
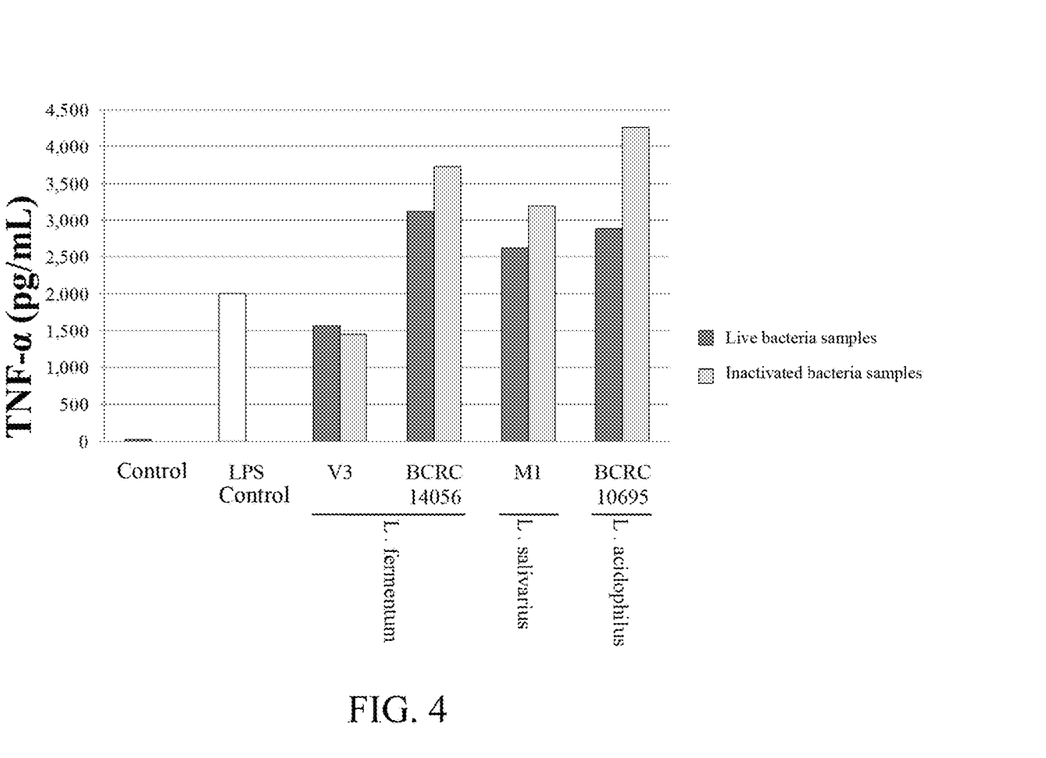
FIG. 4 shows the effect of both the live and inactivated bacteria from *Lactobacillus fermentum* strain V3, *Lactobacillus fermentum* BCRC14056, *Lactobacillus salivarius* M1 and *Lactobacillus acidophilus* BCRC10695 on the inflammatory response.

As shown in FIG. 4, the effect of both the live and dead *Lactobacillus fermentum* strain V3, *Lactobacillus fermentum* BCRC14056, *Lactobacillus salivarius* M1 and *Lactobacillus acidophilus* BCRC10695 on the inflammatory response. BCRC14056, M1, and BCRC10695 promote LPS-induced secretion of TNF-α by THP-1 cells more after the cells died, but the live and death of the bacteria cells of *Lactobacillus fermentum* strain V3 does not change the inhibitory effect on TNF-α.

Example 5 Prevention of Intestinal Inflammation and Colorectal Cancer by *Lactobacillus fermentum* V3

5.1 Design of Animal Experiments

The animals for experiments were five-week-old ICR male mice (28~30 g). The mice for experiments were randomly divided into four groups after one week of pre-cultivation, namely control group, AOMDSS group, Lac.ferm group and Lac.acid group. Each group has 5-8 mice for experiments, and all groups were fed ad libitum with general commercial formula (Laboratory Rodent Diet. 5001). This experiment took the disease prevention model. First, the test sample was administrated, and then the occurrence of colorectal cancer was induced. After the mice were divided into groups, the control group and AOMDSS group were administered PBS by oral gavage, the Lac.ferm group was administered $1 \times 10^8$ CFU/day/mouse of *Lactobacillus fermentum* V3 by oral gavage, and the Lac.acid group was administered $1 \times 10^8$ CFU/day/mouse of *Lactobacillus acidophilus* LA257 by oral gavage for 5 days per week until sacrifice at the 15th week. The colon tissues samples were collected upon sacrifice and stored at −80° C. immediately. The analysis was performed in a 4° C. lysis buffer containing proteinase inhibitors. After homogenization for 30 seconds, it was placed on ice for 30 minutes and then centrifuged at 4° C. (10000 RCF for 30 minutes). The supernatant was centrifuged and the contents of inflammatory cytokines IL-1α and IL-6 were measured by ELISA kit. After feeding the test samples for one week, each mouse in the AOMDSS group, Lac.ferm group and Lac.acid group was intraperitoneally injected with 10 mg/kg body weight of mutagenic agent azoxymethane (AOM). After another week, the drinking water added with 2.5% of the agent causing large intestinal ulcer, i.e. dextran sulfate sodium (DSS), was given for 7 consecutive days, and then ordinary drinking water was provided for 14 days. Afterwards, 2.5% DSS was given again for 7 days to induce colorectal cancer, and finally ordinary drinking water was provided until sacrifice at the 15th week. The control group was intraperitoneally injected with PBS, and DSS was not added to its drinking water.

5.2 Statistical Methods

All data were presented as the mean±SE. The statistical differences between groups were calculated by SPSS 12.0 (SPSS, Inc., Chicago, Ill., USA) and assessed by one-way ANOVA, followed by Tukey's post hoc tests. A two tailed p-value<0.05 was considered statistically significant. $p<0.05$ (*) or $<0.01$ () or $<0.001$ (*).

Figure 5:
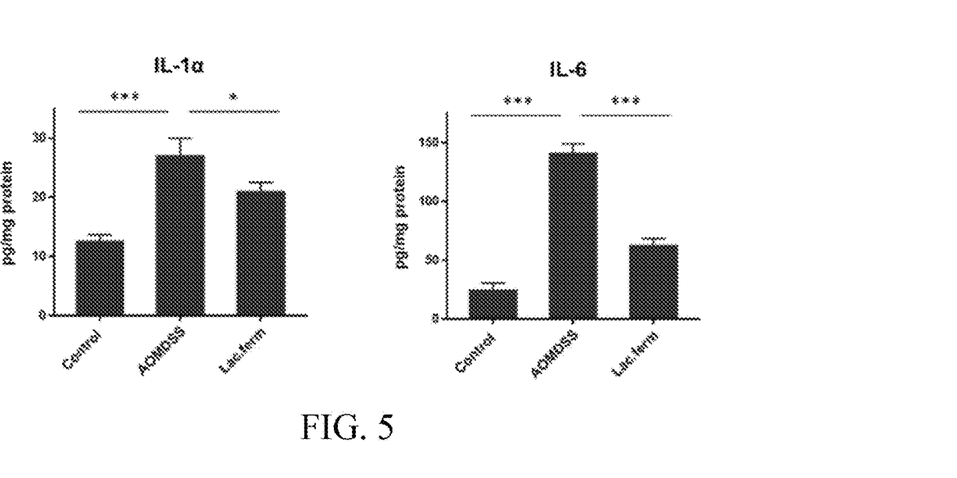
FIG. 5 shows the levels of intestinal inflammatory cytokines IL-1α and IL-6 after the administration of the composition containing the strain V3.

As shown in FIG. 5, as compared with the control group, the levels of intestinal inflammatory cytokines IL-1α and IL-6 in the AOMDSS group were significantly upregulated, while the levels of IL-1α and IL-6 were significantly downregulated after feeding with *Lactobacillus fermentum* V3, indicating that oral administration of the composition containing the strain V3 provides the effect in suppressing intestinal inflammation.

Figure 6:
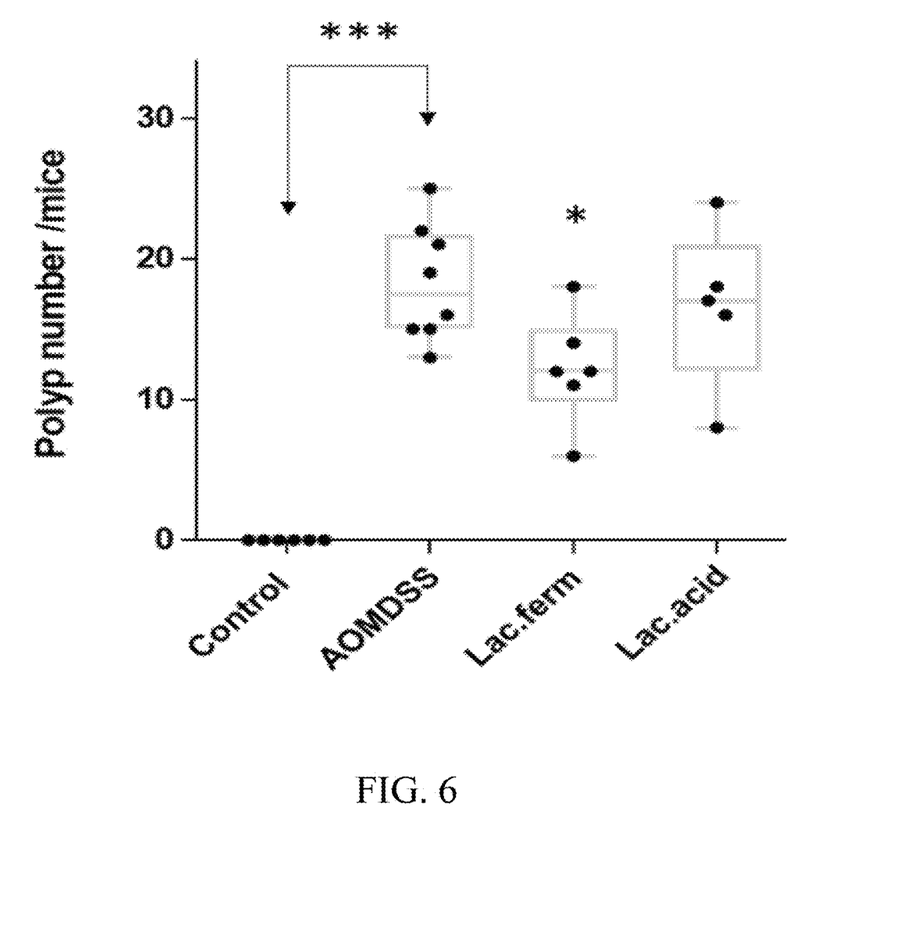
FIG. 6 shows that *Lactobacillus fermentum* strain V3 reduced the number of azoxymethane/dextran sulfate sodium (AOM/DSS)-induced colorectal tumors (*$p<0.05$, **$p<0.01$).

As shown in FIG. 6, compared with the control group, the symptomatic group can significantly induce tumorigenesis of large intestine, indicating that the mutagen can induce tumorigenesis under the inflammatory condition of large intestine. Feeding *Lactobacillus acidophilus* M4 did not affect the number of colorectal tumors, while feeding *Lactobacillus fermentum* strain V3 can significantly reduce the number of colorectal tumors, which means the oral administration of the composition containing the strain V3 provides the effect of preventing colorectal cancer.

Example 6 Regulation of Intestinal Microflora by *Lactobacillus fermentum* V3

6.1 Microbial Analysis of Intestinal Tract

Figure 7:
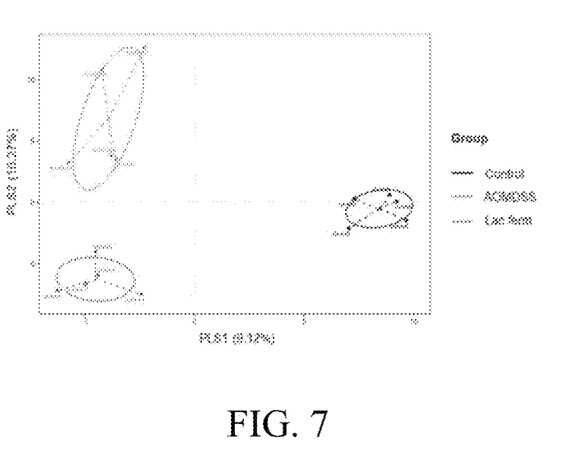
FIG. 7 shows the analysis results of the intestinal microflora by the partial least squares discriminant analysis (PLS-DA) after the administration of the composition containing the strain V3.

Fecal samples were collected from the colon of the experimental mice in Example 5 upon sacrifice under aseptic conditions and immediately stored at −80° C. Bacterial genomic DNA was extracted using the innuSPEED Stool DNA Kit (Analytik Jena AG, Jena, Germany). The primer sequences reported by JG Caporaso et al. (Proceedings of the national academy of sciences, 2011, 108. Supplement 1: 4516-4522.) were used to amplify the V3-V4 region of the 16s rDNA, followed by construction of dual-index barcodes and sequencing adaptors using Illumina DNA library preparation kit (Illumina, San Diego, Calif., USA) under the following conditions: 95° C. for 3 min, 8 cycles of 95° C. (30 s), 55° C. (30 s), and 72° C. (30 s), with a final extension at 72° C. for 5 min. The amplicons were extracted from 2% agarose gels and purified with AMPure XP beads. Barcoded amplicons were pooled (1 nM) and combined with 5% PhiX to use as a spike-in control for Illumina sequencing runs. The library was sequenced on an IlluminaHiSeq2500 platform and paired-end reads (250 bp) were generated. Operational taxonomy units (OTUs) with a similarity of more than 97% were clustered using the UCLUST method. Microbial data analysis performed α- and β-diversity with Quantitative Insights Into Microbial Ecology software (QIIME; version 1.9.1). As shown in FIG. 7 providing the analysis results of the intestinal microflora by the partial least squares discriminant analysis (PLS-DA), the intestinal microflora in the control group, AOMDSS group, and Lac.ferm group (five per group) were significantly different, indicating that oral administration of the composition containing the strain V3 could effectively regulate the intestinal microflora.

Figure 8:
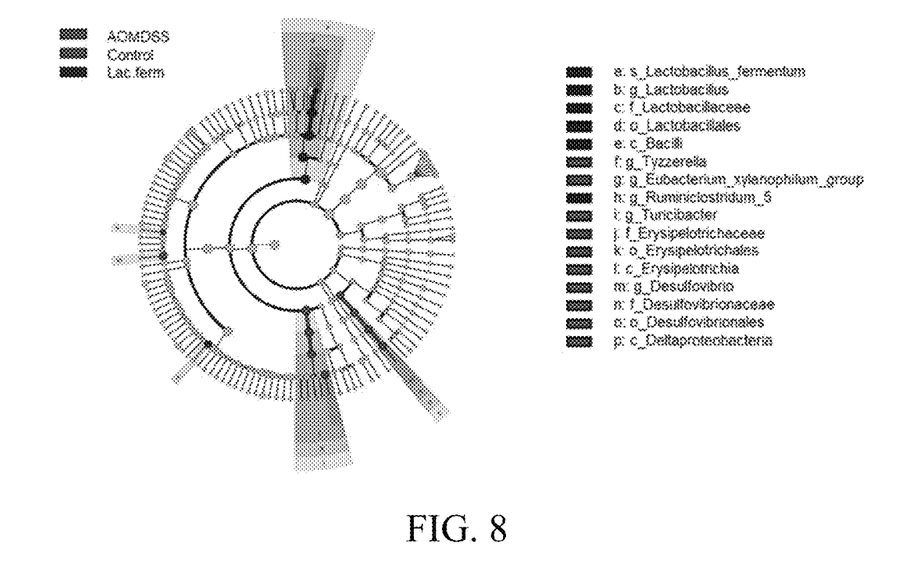
FIG. 8 shows the exploration of the exploration of the specific bacterial taxa characterized in each group, linear discriminant analysis, and size analysis after the AOM/DSS treatment.

FIG. 8, provides the exploration of the specific bacterial taxa characterized in each group, linear discriminant analysis, and size analysis. According to LDA scores (at least >2.0), data showed that five taxa were increased by AOM/DSS treatment, oral V3 can make the five taxa which was increased by AOM/DSS treatment decrease, and six taxa were enriched in the Lac.ferm group, indicating that oral V3 can effectively regulate the intestinal microflora.

Figure 9:
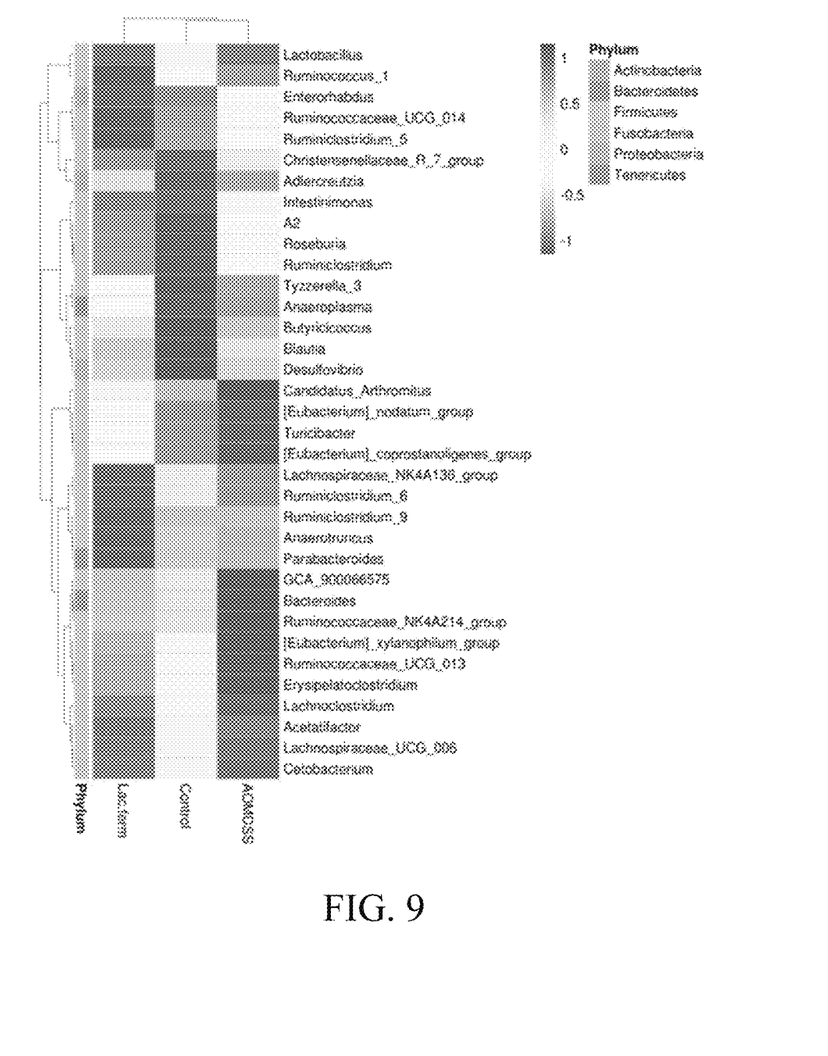
FIG. 9 shows the abundance distribution of the dominant 35 OTUs for genus level as represented as colors in a heatmap among the different groups after AOM/DSS treatment.

As shown in FIG. 9, the abundance distribution of the dominant 35 OTUs for genus level was represented as colors in a heatmap among the different groups. The results demonstrated that AOM/DSS treatment increased the abundance of bacterial taxa such as *Bacteroides, Erysipelatoclostridium*, etc., but reduced that of bacterial taxa such as *Lactobacillus*. However, the strain V3 could reverse most of the microflora changes caused by AOM/DSS, indicating that oral administration of the composition containing the strain V3 effectively recovered from the imbalance of intestinal microflora caused by AOM/DSS and restored the normal intestinal microflora.

Any modifications can be made to the specific embodiments as described above without departing from their broad inventive concepts. Therefore, it should be understood that the present invention is not limited to the disclosed specific embodiments, but is intended to cover modifications within the spirit and scope of the present invention defined by the appended claims.

What is claimed is:

1. A composition in a form of a pharmaceutical composition or a food composition, comprising
heat-inactivated *Lactobacillus fermentum* strain V3 (the strain V3) that is a biological pure culture of *Lactobacillus fermentum* strain V3 (the strain V3) deposited at Deutsche Sammlung von Mikroorganismen and Zellkulturen GmbH, Germany with deposit number DSM33166 on May 28, 2019, and at least one of a pharmaceutically acceptable carrier, a pharmaceutically acceptable excipient, or a suitable drinkable liquid.

2. A method for treating an inflammatory disease in a subject, comprising
administering to the subject a composition in a form of a pharmaceutical composition or a food composition comprising an effective amount of the strain V3 and at least one of a pharmaceutically acceptable carrier, a pharmaceutically acceptable excipient, or a suitable drinkable liquid set forth in claim 1.

3. The method of claim 2, wherein the treatment is through the inhibition of the production of TNF-α.

4. A method for treating a cancer in a subject, comprising administering to the subject a composition in a form of a pharmaceutical composition or a food composition comprising an effective amount of the strain V3 and at least one of a pharmaceutically acceptable carrier, a pharmaceutically acceptable excipient, or a suitable drinkable liquid set forth in claim 1.

5. The method of claim 4, wherein the cancer is selected from the group consisting of colorectal cancer, esophageal cancer and gastric cancer.

\* \* \* \* \*

SEQUENCE LISTING

```
<160> NUMBER OF SEQ ID NOS: 1

<210> SEQ ID NO 1
<211> LENGTH: 491
<212> TYPE: DNA
<213> ORGANISM: Lactobacillus fermentum
<220> FEATURE:
<221> NAME/KEY: misc_feature
<222> LOCATION: (490)..(490)
<223> OTHER INFORMATION: n is a, c, g, or t

<400> SEQUENCE: 1
tgcagtcgaa cgcgttggcc caattgattg atggtgcttg cacctgattg attttggtcg      60
ccaacgagtg gcggacgggt gagtaacacg taggtaacct gcccagaagc gggggacaac     120
atttggaaac agatgctaat accgcataac agcgttgttc gcatgaacaa cgcttaaaag     180
atggcttctc gctatcactt ctggatggac ctgcggtgca ttagcttgtt ggtggggtaa     240
cggcctacca aggcgatgat gcatagccga gttgagagac tgatcggcca caatgggact     300
gagacacggc ccatactcct acgggaggca gcagtaggga atcttccaca atgggcgcaa     360
gcctgatgga gcaacaccgc gtgagtgaag aagggtttcg gctcgtaaag ctctgttgtt     420
aaagaagaac acgtatgaga gtaactgttc atacgttgac ggtatttaac cagaaagtca     480
cggctaacdn a                                                         491
```